(12) United States Patent
Jin et al.

(10) Patent No.: US 9,155,685 B2
(45) Date of Patent: Oct. 13, 2015

(54) LOW STRESS FLOWABLE DENTAL COMPOSITION

(75) Inventors: Xiaoming Jin, Middletown, DE (US); Louis Bertrand, Lewes, DE (US); Qizhou Dai, Dover, DE (US); Michael T. O'Connor, Leesburg, VA (US); Paul D. Hammesfahr, Lewes, DE (US); Bernard Koltisko, Milton, DE (US)

(73) Assignee: DENTSPLY INTERNATIONAL INC., York, PA (US)

( * ) Notice: Subject to any disclaimer, the term of this patent is extended or adjusted under 35 U.S.C. 154(b) by 547 days.

(21) Appl. No.: 13/098,508

(22) Filed: May 2, 2011

(65) Prior Publication Data

US 2011/0315928 A1 Dec. 29, 2011

Related U.S. Application Data

(60) Provisional application No. 61/343,744, filed on May 3, 2010, provisional application No. 61/363,800, filed on Jul. 13, 2010.

(51) Int. Cl.
- *A61K 6/083* (2006.01)
- *A61K 6/00* (2006.01)
- *A61K 6/02* (2006.01)

(52) U.S. Cl.
CPC .............. *A61K 6/0008* (2013.01); *A61K 6/0088* (2013.01); *A61K 6/0091* (2013.01); *A61K 6/0215* (2013.01); *A61K 6/0255* (2013.01); *A61K 6/0002* (2013.01); *A61K 6/083* (2013.01)

(58) Field of Classification Search
CPC ....... A61K 6/08; A61K 6/083; A61K 6/0002; A61K 6/0088; A61K 6/0091; A61L 27/16
USPC ........................................................ 523/115
See application file for complete search history.

(56) References Cited

U.S. PATENT DOCUMENTS

| | | | |
|---|---|---|---|
| 4,922,004 A * | 5/1990 | Kohler et al. | 560/221 |
| 6,030,606 A | 2/2000 | Holmes | |
| 7,544,721 B2 | 6/2009 | Gaud et al. | |
| 2008/0076848 A1 * | 3/2008 | Jin et al. | 522/162 |
| 2008/0076853 A1 * | 3/2008 | Jin et al. | 523/116 |

FOREIGN PATENT DOCUMENTS

EP 2199273 A1 * 6/2010 ........... C07D 335/16

OTHER PUBLICATIONS

Y. M. Paushkin et al, Organic Polymeric Semiconductors, John Wiley & Sons, New York, 1974.
J.M. Pearson, Pure and Appl. Chem., 49, 463-477 (1977).

* cited by examiner

*Primary Examiner* — Michael Pepitone
(74) *Attorney, Agent, or Firm* — Leana Levin; Douglas J. Hura; David A. Zdurne

(57) ABSTRACT

Disclosed herein are low viscosity and low stress dental compositions comprising at least one low stress polymerizable resin and at least one filler. The dental compositions described herein have high depth of cure and self-leveling characteristics and are capable of bulk application.

12 Claims, 1 Drawing Sheet

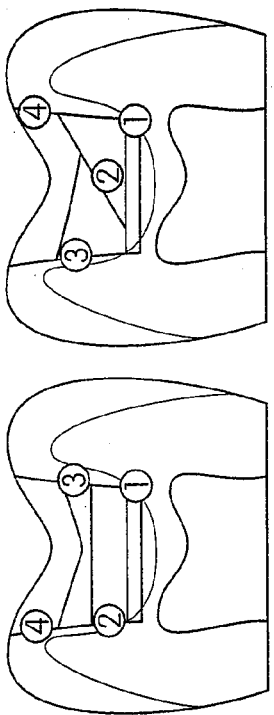

LOW STRESS FLOWABLE DENTAL COMPOSITION

This application claims priority to Provisional Application No. 61/343,744, filed May 3, 2010, and Provisional Application No. 61/363,800, filed Jul. 13, 2010.

BACKGROUND

Highly cross-linked polymers have been studied widely as matrices for composites, foamed structures, structural adhesives, insulators for electronic packaging, etc. The densely cross-linked structures are the basis of superior mechanical properties such as high modulus, high fracture strength, and solvent resistance. However, these materials are irreversibly damaged by high stresses due to the formation and propagation of cracks. Polymerization stress is originated from polymerization shrinkage in combination with the limited chain mobility. Which eventually leads to contraction stress concentration and gradually such a trapped stress would release and caused microscopically the damage in certain weak zone like interfacial areas. Macroscopically it is reflected as debonding, cracking, or the like. Similarly, the origin of the contraction stress in current adhesive restorations is also attributed to the restrained shrinkage while a resin composite is curing, which is also highly dependent on the configuration of the restoration. Furthermore, non-homogeneous deformations during functional loading can damage the interface as well as the coherence of the material. Various approaches have been explored by limiting the overall stress generation either from the restorative materials, or by minimizing a direct stress concentration at the restored interface. It included, for example, new resin, new resin chemistry, new filler, new curing process, new bonding agent, and even new procedure.

There has been much attention paid to new resin matrix development that could offer low polymerization shrinkage and shrinkage stress. For example, various structure and geometry derivatives of (meth)acrylate-based resin systems; non-(meth)acrylates resin systems, non-radical-based resin system. In addition, for light curable, low shrink dental composites, not only new resin systems and new photoinitiators, new filler and filter's surface modification have also been extensively explored, such as filler with various particle size and size distribution, from nanometer to micrometer, different shape, irregular as milled or spherical as-made. It can also be different in composition like inorganic, organic, hybrid. Although an incremental improvement has been achieved with each approach and/or their mutual contribution, polymerization stress is still the biggest challenge in cured network systems.

Dental composite is formulated by using organic or hybrid resin matrix, inorganic or hybrid fillers, and some other ingredients such as initiator, stabilizer, pigments, etc., so as to provide the necessary esthetic, physical and mechanical property for tooth restoration. It is well known that polymerization shrinkage from cured dental composite is one of dental clinicians' main concerns when placing direct, posterior, resin-based composite restorations. Although there are evolving improvements associated with resin-based composite materials, dental adhesives, filling techniques and light curing have improved their predictability, the shrinkage problems remain. In fact, it is the stress associated to polymerization shrinkage that threatens marginal integrity and lead to marginal gap formation and microleakage, which may contribute to marginal staining, post-operative sensitivity, secondary caries, and pulpal pathology.

A common approach to reduce the polymerization shrinkage of dental composite is to increase the filler loading, especially for posterior restoration. However, the higher viscosity of these highly filled composites may not adapt as well to cavity preparations. It has been demonstrated that to initially place a flowable composites which, with less filler content, have greater flexibility, could reduce microleakage than direct application of microhybrid and packable composite restorations, but this benefit may be offset by the increasing polymerization shrinkage for the flowable composite itself. Therefore, it is also highly desirable to develop low shrinkage, especially low curing stress flowable composite, in order to really reduce microleakage as mentioned above.

The challenge in developing any dental composite is to balance the overall performance, including esthetic appearance, handling character as well, in addition to low curing stress and necessary mechanical strength. Unfortunately, superior mechanical strength usually is a result of increasing cross-linking density, from which an unwanted polymerization shrinkage and shrinkage stress always accompany. There is increasing effort to develop new resin systems in the attempt to minimize such shrinkage and stress accordingly. For example, reducing the polymerizable groups in the resin matrix by designing resin monomer with different size and shape indeed work well to some extent in this regard. However, it is usually resulted in decreasing mechanical strength and losing certain handling characteristic because of the limited molecular chain mobility and the limited polymerization conversion. In addition the shrinkage can also be reduced by using special filters which allow an increase in filler loading without compromising too much in handling property. Even so, the curing stress from most of flowable composites remains substantially high. Obviously, it is highly desirable to develop flowable dental composition with low curing stress.

SUMMARY

Disclosed herein is a dental composition, comprising an oligomeric resin, a second resin, and a filler, wherein the dental composition has an initial viscosity of under a low shear stress of about 10 Pa in a range of from about 10 Pa·s to about 1000 Pa·s at about 35° C., wherein the dental composition has a depth of cure of from about 3 mm to about 6 mm, wherein the dental composition has a polymerization stress of from about 0.5 MPa to about 2 MPa, and wherein the dental composition has a shrinkage stress of from about 0.8 Mpa to about 2.2 MPa.

Further disclosed herein is a method of making a dental composition, comprising forming an oligomeric resin having a photoresponsive moiety by combining an (meth)acrylate, a polyisocyanate, and a reactive photoinitiator, combining the oligomeric resin and a second resin to form a compound resin, combining the compound resin with a filler to form the dental composition, wherein the dental composition has an initial viscosity of under a low shear stress of about 10 Pa in a range of from about 10 Pa·s to about 1000 Pa·s at about 35° C., wherein the dental composition has a depth of cure of from about 3 mm to about 6 mm, wherein the dental composition has a polymerization stress of from about 0.5 MPa to about 2 MPa, and wherein the dental composition has a shrinkage stress of, from about 0.8 Mpa to about 2.2 MPa.

It is the ultimate goal to offer a low polymerization stress flowable composition for use in bulk restoration for minimizing the defects caused by a known layering placement procedure, which is required for high polymerization stress restoratives. Obviously it should be even more desirable to develop low polymerization stress flowable composite with high depth of cure, which would allow a bulk placement and bulk curing.

It is also highly desirable for such low polymerization stress flowable composite with high depth of cure to offer an additional rheological feature such as self-leveling, which would allow smooth and better placement without any manipulation.

BRIEF DESCRIPTION OF THE DRAWINGS

FIG. 1 pictorially demonstrates the difference in filling a dental cavity using a conventional dental composite as compared to the dental composite disclosed herein.

DETAILED DESCRIPTION

Disclosed herein is a composition suitably for use as a dental restorative material. The composition includes at least a resin and a filler. The composition may optionally include at least one of a photoinitiator, a stabilizer, a fluorescent agent and a colorant. The composition having disclosed herein demonstrates improved dental restorative characteristics, such as an ability to bulk fill and being self-leveling.

Resins suitable for use in the composition disclosed herein include polymerizable resins. Suitable polymerizable compositions may include photopolymerizable components that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth) acrylamide; urethane (meth)acrylates; the bis-(meth)acrylates of polyethylene glycols (preferably of molecular weight 200-500), copolymerizable mixtures of acrylated monomers, acrylated oligomers, and poly(ethylenically unsaturated) carbamoyl isocyanurates; and vinyl compounds such as styrene, diallyl phthalate, divinyl succinate, divinyl adipate and divinyl phthalate. Other suitable free radically polymerizable compounds include siloxane-functional (meth)acrylates, and fluoropolymer-functional (meth)acrylates. Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl(meth)acrylate and 2-hydroxypropyl(meth)acrylate; glycerol mono- or di-(meth) acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis [4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

Other photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Preferred photopolymerizable resins are derived from polyisocyanate compounds useful in preparing resins suitable for the dental composition described herein comprise isocyanate radicals attached to the multivalent organic group (R', the "residue" of a polyisocyanate)) that can comprise a multivalent aliphatic, alicyclic, or aromatic moiety; or a multivalent aliphatic, alicyclic or aromatic moiety attached to a biuret, an isocyanurate, or a uretdione, or mixtures thereof. Preferred polyfunctional isocyanate compounds contain an average of at least two isocyanate (—NCO) radicals. Compounds containing at least two —NCO radicals are preferably comprised of di- or trivalent aliphatic, alicyclic, araliphatic, or aromatic groups to which the —NCO radicals are attached. Aliphatic di- or trivalent groups are preferred.

Representative examples of suitable polyisocyanate compounds include isocyanate functional derivatives of the polyisocyanate compounds as defined herein. Examples of derivatives include, but are not limited to, those selected from the group consisting of ureas, biurets, allophanates, dimers and trimers (such as uretdiones and isocyanurates) of isocyanate compounds, and mixtures thereof. Any suitable organic polyisocyanate, such as an aliphatic, alicyclic, araliphatic, or aromatic polyisocyanate, may be used either singly or in mixtures of two or more.

The aliphatic polyisocyanate compounds generally provide better light stability than the aromatic compounds. Aromatic polyisocyanate compounds, on the other hand, are generally more economical and reactive toward nucleophiles than are aliphatic polyisocyanate compounds. Suitable aromatic polyisocyanate compounds include, but are not limited to, those selected from the group consisting of 2,4-toluene diisocyanate (TDI), 2,6-toluene diisocyanate, an adduct of TDI with trimethylolpropane (available as Desmodur™ CB from Bayer Corporation, Pittsburgh, Pa.), the isocyanurate trimer of TDI (available as Desmodur™ IL from Bayer Corporation, Pittsburgh, Pa.), diphenylmethane 4,4'-diisocyanate (MDI), diphenylmethane 2,4'-diisocyanate, 1,5-diisocyanato-naphthalene, 1,4-phenylene diisocyanate, 1,3-phenylene diisocyanate, 1-methyoxy-2,4-phenylene diisocyanate, 1-chlorophenyl-2,4-diisocyanate, and mixtures thereof.

Examples of useful alicyclic polyisocyanate compounds include, but are not limited to, those selected from the group consisting of dicyclohexylmethane diisocyanate ($H_{12}$MDI, commercially available as Desmodur™ available from Bayer Corporation, Pittsburgh, Pa.), 4,4'-isopropyl-bis(cyclohexylisocyanate), isophorone diisocyanate (IPDI), cyclobutane-1,3-diisocyanate, cyclohexane 1,3-diisocyanate, cyclohexane 1,4-diisocyanate (CNDI), 1,4-cyclohexanebis(methylene isocyanate) (BDI), dimmer acid diisocyanate (available from Bayer), 1,3-bis(isocyanatomethyl)cyclohexane (H₆XDI), 3-isocyanatomethyl-3,5,5-trimethylcyclohexyl isocyanate, and mixtures thereof.

Examples of useful aliphatic polyisocyanate compounds include, but are not limited to, those selected from the group consisting of tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, 2,2,4-trimethyl-hexamethylene diisocyanate (TMDI), 2-methyl-1,5-pentamethylene diisocyanate, dimer diisocyanate, the urea of hexamethylene diisocyanate, the biuret of hexamethylene 1,6-diisocyanate (HDI), the isocyanurate of HDI, a blend of the isocyanurate of HDI and the uretdione of HDI, and mixtures thereof.

Examples of useful araliphatic polyisocyanates include, but are not limited to, those selected from the group consisting of m-tetramethyl xylylene diisocyanate (m-TMXDI), p-tetramethyl xylylene diisocyanate (p-TMXDI), 1,4-xylylene diisocyanate (XDI), 1,3-xylylene diisocyanate, p-(1-isocyanatoethyl)phenyl isocyanate, m-(3-isocyanatobutyl)phenyl isocyanate, 4-(2-isocyanatocyclohexyl-methyl)phenyl isocyanate, and mixtures thereof.

Examples of useful arylene polyisocyanates include, but are not limited to, xylylene-1,4-diisocyanate (p-XDI), xylylene-1,3-diisocyanate (m-XDI), m-pheylene diisocyanate, p-pheylene diisocyanate, toluene-2,6-diisocyanate (2,6-TDI), toluene-2,4-diisocyanate (2,4-TDI), mesitylene diisocyanate, durylene diisocyanate, benzidene diisocyanate, 1-methyl phenylene-2,4-diisocyanate naphthylene-1,4-diisocyanate, 1,2,4-benzene triisocyanate, 4,4'-diisocyanato diphenyl methane (MDI), 3,3'-dimethyl-4,4'-diisocyanato diphenyl methane, 4,4'-diphenyl propane diisocyanate, dianisidine diisocyanate, m-tetramethylenexylene diisocyanate (TMXDI).

The more suitable resins for use in the dental composition described herein include a (meth)acrylate urethane oligomer made of an acrylate, a polyisocyanate and a photoresponsive moiety derived from any conventional initiator. Suitable examples of the acrylate and polyisocyanate or more fully described herein, and the photoresponsive moiety may be derived from any conventional initiator described herein so that a suitable oligomeric resin having such a moiety is created.

The most oligomeric resins may have a general structure of:

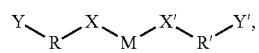

where M is a photoresponsive moiety, where X or X' is a same or different direct linkage or ether, thioether, ester, thioester, urea, urethane, carbonate, or the like, where R or R' is a same or different alkyl, alicyclic, aromatic residues, substitute aromatic residues, or the like, and where Y or Y' is a same or different polymerizable groups such as vinyl, vinylether, acrylic, methacrylic, epoxide or the like.

More specific examples of suitable oligomeric resins include:

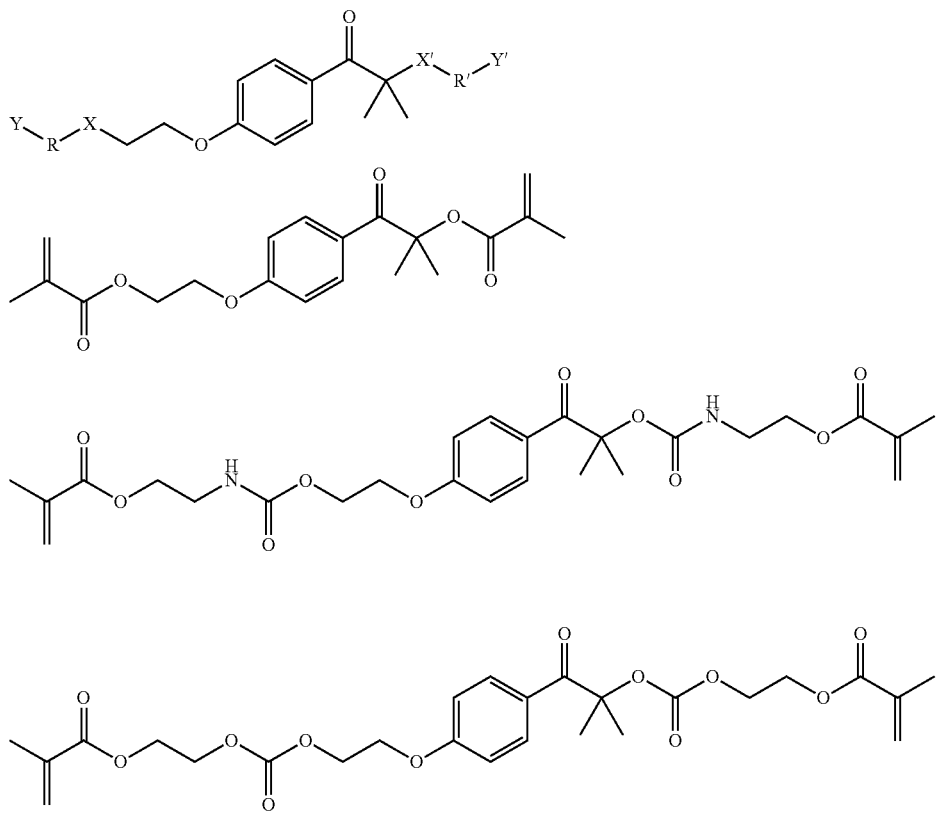

-continued

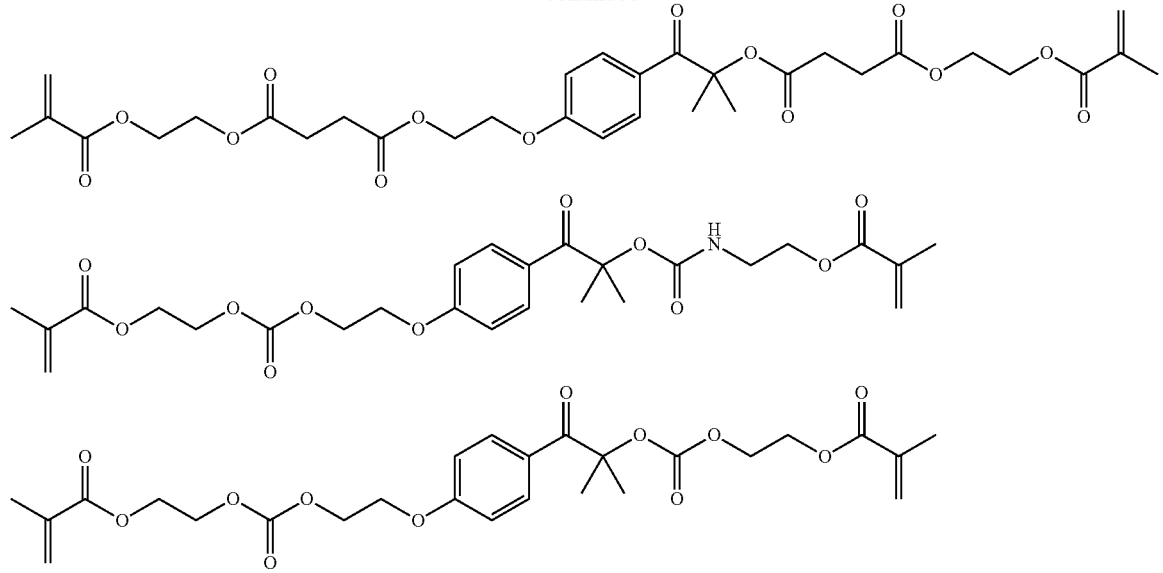

In embodiments, the oligomeric resin is an oligomer of an acrylate, a polyisocyanate compound and a photoinitiator. The acrylate may be present in the oligomeric resin in amounts of from about 25 weight percent to about 60 weight percent, such as from about 30 weight percent to about 55 weight percent or from about 35 weight percent to about 50 weight percent. The polyisocyanate may be present in the oligomeric resin in amounts of from about 30 weight percent to about 60 weight percent, such as from about 35 weight percent to about 55 weight percent or from about 40 weight percent to about 50 weight percent. The photoinitiator may be present in the oligomeric resin in amounts of from about 25 weight percent to about 60 weight percent, such as from about 30 weight percent to about 55 weight percent or from about 35 weight percent to about 50 weight percent.

The total amount of resin present in the dental composition described herein is from about 10 weight percent to about 95 weight percent of the dental composition, such as from about 15 weight percent to about 50 weight percent or about 20 weight percent to about 45 weight percent or from about 25 weight percent to about 40 weight percent of the dental composition.

The compositions of the present disclosure can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 0.1 micrometers, and more preferably less than 0.075 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers; and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.).

Examples of suitable organic filler particles include filled or unfilled pulverized polycarbonates, polyepoxides, and the like.

Suitable non-acid-reactive filler particles are quartz, submicron silica, and non-vitreous microparticles. Mixtures of these non-acid-reactive fillers are also contemplated, as well as combination fillers made from organic and inorganic materials. Silane-treated zirconia-silica (Zr—Si) filler is suitable in certain embodiments.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. In embodiments, the filler may be at least one type of FAS glass. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Further suitable filler components include nanosized silica particles, nanosized metal oxide particles, and combinations thereof.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., wherein the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition.

The total amount of filler present in the dental composition described herein is from about 5 weight percent to about 90 weight percent of the dental composition, such as from about 45 weight percent to about 90 weight percent or about 50 weight percent to about 85 weight percent or from about 60 weight percent to about 75 weight percent of the dental composition.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound. Preferred iodonium salts are the diaryliodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm), such as 1-[4-(2-hydroxyethoxy)-phenyl]-2-hydroxy-2-methyl-1-propane-1-one (IRGACURE 2959, BASF Corp., Charlotte, N.C.). More preferred compounds are alpha diketones that have some light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins.

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides.

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, BASF Corp., Charlotte, N.C.), bis(2,6-dimethoxybenzoyl)-(2,4,4-trimethylpentyl) phosphine oxide (CGI 403, BASF Corp., Charlotte, N.C.), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, BASF Corp., Charlotte, N.C.), a 1:1 mixture, by weight, of bis(2,4,6-trimethylbenzoyl)phenylphosphine oxide and 2-hydroxy-2-methyl-1-phenylpropane-1-one (DAROCUR 4265, BASF Corp., Charlotte, N.C.), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

The total amount of optional photoinitiator, not including any photoinitiator that may be present in the resin compound, present in the dental composition described herein is from about 0 weight percent to about 5 weight percent of the dental composition, such as from about 0.01 weight percent to about 3 weight percent or from about 0.07 to about 1 weight percent or from about 0.1 weight percent to about 0.02 weight percent of the dental composition.

Examples of suitable sensitizers include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha-diketones), ketocoumarins, aminoarylketones, and p-substituted aminostyryl ketone compounds are preferred sensitizers. For applications requiring deep cure of epoxy-containing materials (e.g., cure of highly filled composites), it is preferred to employ sensitizers having an extinction coefficient below about 100 (mole$^{-1}$ cm$^{-1}$, more preferably about or below 100 mole$^{-1}$ cm$^{-1}$, at the desired wavelength of irradiation for photopolymerization. The alpha-diketones are an example of a class of sensitizers having this property, and are particularly preferred for dental applications.

Examples of suitable visible light sensitizers include camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2-cyclohexanedione.

The total amount of optional stabilizer present in the dental composition described herein may be from about 0 weight percent to about 5 weight percent of the dental composition, such as from about 0.01 weight percent to about 2 weight percent or from about 0.1 weight percent to about 1 weight percent of the dental composition.

The composition disclosed herein may optionally include a fluorescent agent, such as 1,2-benzenedicarboxylic acid 2,5-dihydroxydiethyl ester (flublau).

The total amount of optional fluorescent agent present in the dental composition described herein may be from about 0 weight percent to about 3 weight percent of the dental composition, such as from about 0.01 weight percent to about 1 weight percent or from about 0.03 weight percent to about 0.01 weight percent of the dental composition.

Colorants suitable for use in the composition disclosed herein include dyes and pigments. Suitable pigments include, but are not limited to, titanium dioxide, strontium titanate, barium titanate, zinc oxide, zinc sulfide, zinc selenide, cadmium sulfide, cadmium selenide, cadmium telluride, or combinations thereof. Suitable organic pigments include, but are not limited to, phthalocyanine blue (pigment blue 15), copper polychlorophthalocyanine green (pigment green 7), copper polybromochlorophthalocyanine (pigment green 36), perylene scarlet (vat red 29), perylene vermillion (pigment red 23), perylene maroon, perylene Bordeaux, and perylene dianhydride (perylene red) as those described in "Pigments-Inorganic" and "Pigments-Organic" in Kirk-Othmer Encyclopedia of Chemical Technology, Third ed., Volume 17, pp. 788-817, John Wiley and Sons, New York, 1982. The organic pigments can also be semiconducting polymers as described by Y. M. Paushkin et al., Organic Polymeric Semiconductors, John Wiley & Sons, New York, 1974 and by J. M. Pearson, Pure and Appl. Chem., 49, 463-477 (1977).

The total amount of optional colorant present in the dental composition described herein may be from about 0 weight percent to about 5 weight percent of the dental composition, such as from about 0 weight percent to about 3 weight percent or from about 0 weight percent to about 1 weight percent of the dental composition.

The dental compositions disclosed herein may be made by any suitable method. As an example, the dental compositions disclosed herein may be made by first forming the oligomeric resin having a photoinitiator moiety as described herein by any known means. This oligomeric resin can be used alone or can then be combined with any additional resins described herein. In other embodiments, the resin compound can be derived from any combination of resins described herein. The combination of resins is then combined with the filler disclosed herein to form a compound. This compound is then combined with the optional photoinitiator, stabilizer, fluorescent agent and/or colorant. These components may be combined or mixed by any suitable method to form the dental composition disclosed herein.

The dental composition described herein exhibits improved characteristics as compared to other dental restorative compositions known in the art. In embodiments, the dental restorative composition described herein exhibits the desired characteristics of selectable viscosity prior to cure, low shrinkage upon cure, improved depth of cure, low polymerization stress and other good mechanical properties. Key features of a composition having the oligomeric resin described herein include low shrinkage stress, low polymerization stress, low viscosity and a high depth of cure.

The dental composition disclosed herein provides flowable composites with an exceptionally low polymerization stress of from about 0.5 MPa to about 2 MPa, such as from about 0.7 MPa to about 1.5 MPA or from about 0.9 MPa to about 1.3 MPa. Such low polymerization stress values are a significant improvement as compared to known, commercial products, such as ESTHETXFLOW® having a polymerization stress of 3.4 MPa and DYRACTFLOW® having a polymerization stress of 4.6 MPa. In addition to the low polymerization stress, dental compositions disclosed herein provide composites with a low shrinkage stress of from about 0.8 MPa to about 2.2 MPa, such as from about 1.0 MPa to about 2.0 MPa or from about 1.3 MPa to about 1.7 MPa.

In addition to having the low polymerization stress, the dental composition described herein also has a low viscosity prior to cure which results in improved handling, self-leveling and adaptive rheological properties. Because of the improved depth of cure, bulk placement of the described dental composition may be achieved. As pictorially demonstrated in FIG. 1, in the prior art, because of various short comings, it has been necessary to apply restoratives in small quantities and cure each layer before the next layer would be placed, for example, conventional restoratives would be placed about 2 mm into a dental cavity followed by curing and placement of a second layer onto the first layer. At no time would more than 2 mm of conventional dental restorative be placed in a dental cavity at one time. The interface between these layers in conventional dental restoratives compositions is a potential problem area and a great care must be taken by the dental practitioner in such multi-layer applications so as to avoid cracking, debonding or the like, which could lead to catastrophic failure of the restorative.

In contrast to these conventional dental restorative compositions, the dental composition disclosed herein may be placed in a dental cavity in layers of 3 mm or more, such as from about 3 mm to about 6 mm, or from about 3.5 mm to about 6 mm or from about 3.5 mm to about 5.5 mm or from 4 mm to about 6 mm or from about 4 mm to about 5 mm. This bulk placement is possible because of the low polymerization stress upon curing of the dental composition disclosed herein. This bulk placement may also be referred to as depth of cure as the dental composite is capable of being cured at a significantly greater depth and placement than other known dental compositions.

In embodiments, the dental restorative composition may be adjusted to be self-leveling, stackable or anything in between, while continuing to exhibit low polymerization stress. For exemplary purposes, if the composition disclosed herein has an initial viscosity under low shear stress of about 10 Pa in a range of from about 10 Pa·s to about 1000 Pa·s at about 35° C., and its response to change in shear stress of from about 10 Pa to about 1000 Pa is about 1 to about 95 percent reduction, such a composition will be referred to as being self-leveling. If the initial viscosity under low shear stress of about 10 Pa in a range of from about 10 Pa·s to about 1000 Pa·s at about 35° C., and its response to change in shear force is from about 1000 Pa to about 5000 Pa is about 95 to about 99 percent reduction, such a composition will be referred to as being semi-stackable. If the initial viscosity under low shear stress of about 10 Pa in a range of from about 10 Pa·s to about 1000 Pa·s at about 35° C., and its response to change in shear stress is from about 5000 Pa to about 150000 Pa is about 99 to about 100 percent reduction, such a composition will be referred to as being stackable.

A self-leveling composition according the present disclosure has an initial viscosity under low shear stress of 10 Pa range 50 to 500 Pa·s at 35° C., and its response to change in shear stress of 10 Pa to 1000 Pa is 5 to 80 percent reduction. A further self-leveling composition according to the present disclosure has an initial viscosity under low shear stress of 10 Pa range 100 to 200 Pa·s at 35° C., and its response to change in shear stress of 10 Pa to 1000 Pa is 10 to 70 percent reduction. A self-leveling feature of a direct dental restorative is helpful to improve the adaptation or the contact against the prepared target site or cavity walls in a tooth to be restored. With the filler composition described herein, a variety of depth of cure would be achievable by the resulting low viscosity and low stress composite, depending upon the selected opacity of the composition.

By appropriately selecting other component of the disclosed product, the stackability and other handling properties of the disclosed dental composition may be pre-selected, while upon curing the composition disclosed herein exhibits improved stress characteristics, such as a low polymerization stress of from about 0.5 MPa to about 2 MPa, such as from about 0.7 MPa to about 1.5 MPA or from about 0.9 MPa to about 1.3 MPa. While stacking and self-leveling characteristics are individually known in the prior art, a dental composition exhibiting both characteristics in addition to a low polymerization stress and improved depth has not been known in the past.

The dental composition disclosed herein has been found to achieve an opacity of less than or equal to about 70, less than or equal to about 50 or less than or equal to about 45. The actual or target opacity will depend upon the end use of the dental composition. The opacity number as is conventional in the art is based upon the contrast ratio. By achieving such a low opacity, the depth of cure is also improved.

The depth of cure may be as high as 3 mm or more, such as from about 3 mm to about 6 mm, or from about 3.5 mm to about 6 mm or from about 3.5 mm to about 5.5 mm or from 4 mm to about 6 mm or from about 4 mm to about 5 mm. While the composition according to the present disclosure may be photocured, and thus improved with respect to its depth of cure, it will also be appreciated that the composition disclosed herein can also be chemically cured, thermally cured, redox, any other forms of irradiation, such as ultrasonic, microwave or the like, any combination of all of these or the like. In such a case, opacity is not necessarily critical so materials with higher opacities are still within the scope of the present disclosure.

It will be appreciated that the composition described herein provides a dental restorative composition with selective viscosity such as low viscosity, that is, a flowable viscosity, yet exhibits low polymerization stress of from about 0.5 MPa to about 2 MPa, such as from about 0.7 MPa to about 1.5 MPA or from about 0.9 MPa to about 1.3 MPa, with a high depth of cure of 3 mm or more, such as from about 3 mm to about 6 mm, or from about 3.5 mm to about 6 mm or from about 3.5 mm to about 5.5 mm or from 4 mm to about 6 mm or from about 4 mm to about 5 mm, and which is capable of application in bulk placement procedures of 4 mm or more, such as from 4 mm to about 6 mm. In addition, the composition described herein also yields unique selective rheological behavior, such as self-leveling and/or stackable properties, which is a benefit in various dental procedures.

In order to demonstrate the effectiveness of the composition disclosed herein, a number of exemplary and control samples were obtained and tested as will now be reported. Commercially available materials may be referred to by their respective trademarks or the like.

Description on Test Method:

Flexural strength and modulus: tested according to ISO 4049, 2×2×25 mm specimens were cured by three overlapped spot curing with Spectrum 800 with 13 mm light guide at 800 mw/cm$^2$, 20" for each spot on one side only. The cured specimens (6-10) were placed in DI water and stored at 37° C. for 24 hrs, then were sanded prior to the test at room temperature.

Compressive strength and modulus: tested according to ISO 9917, which is actually for water-based cements since ISO 4049 does not specify for compressive strength. ⌀ 14×6 mm glass slave as mold for specimen preparation. It was cured by Spectrum 800 at 800 mw/cm$^2$ from both top and bottom for 20" each. The cured specimens were stored in DI water at 37° C. for 24 hrs, and they were sanded prior to the test at room temperature.

Polymerization Shrinkage: calculated from the density change before and after curing, which were measured by helium pycnometer at room temperature. 3 pieces of round disc samples from a ⌀ 10×2 mm Teflon mold. It was presses between Mylar films and cured by Spectrum 800 at 800 mw/cm$^2$ for 20 seconds from top and bottom sides, respectively. The cured specimen is stored at room temperature for 24 hrs prior to the density measurement.

Shrinkage Stress: measured by using NIST/ADA's tensometer. Specimen with 2.25 mm in thickness (c-factor as 1.33) is cured for 60 seconds by DENTSPLY/Caulk's QHL light at 550 mw/cm2. The total stress at the 60$^{th}$ minute is taken to rank different materials.

ISO Depth of Cure:

Depth of Cure: Based on ISO 4049. The restorative material was light cured for 20 seconds in a stainless steel mold with a cylindrical chamber, 4 mm in diameter and 10 mm long and a Whatman No. 1 filter paper as background with a Spectrum 800 halogen light at a light intensity of 550 mW/cm$^2$. The uncured side was scraped away using a plastic spatula and the thickness of the remaining, cured composite was measured by a micrometer. The depth of cure was the remaining thickness divided by two.

Opacity: A circular mold, with internal dimensions 30 mm diameter×1 mm height, was placed on a glass plate and slightly overfilled with composite. The second glass plate was positioned on top of the paste covering the mold. The two plates and mold were secured together using binder clips and the composite was light cured in Triad 2000 for 2 minutes on each side. The specimens were removed from the molds. The opacity value was measured as the contrast ratio of black to white backgrounds in the CIE L*a*b* scale on a Greta Macbeth Color-EYE 3100.

Viscosity: TA Instruments AR1000 Rheometer was used to study viscosity of uncured pastes. 2-3 gram of paste was loaded under 40 mm cone-plate geometry and was swept by shear stress from 10 Pa to 2000 Pa at 35° C. 10 data points were collected for each decade.

As used in the Examples and throughout the present application, the term "base resin" refers to the oligomeric resin described herein, the term "Formulated resin" refers to the resin composition that includes the oligomeric resin and another resin utilized in the dental composition disclosed herein, and "Formulated composites" refers to the dental composition having a resin and filler, as disclosed herein.

The following abbreviations are used in the examples.
BisGMA: 2,2-bis(4-(3-methacryloyloxy-2-hydroxypropoxy)-phenyl)propane
Irgacure 2959(HP): 4-(2-hydroxyethoxy)-phenyl-2-hydroxy-2-methyl-2-propanone
HEMA: 2-hydroxyethyl methacrylate
HEPA: 2-hydroxypropyl methacrylate
TEGDMA: triethylene glycol dimethacrylate
UDMA: di(methacryloxyethyl)trimethyl-1,6-hexaethylene-diurethane
HEMASA: mono-2-(methacryl-oxy)ethyl-succinate
TMDI: 2,2,4(2,4,4)-trimethyl-1,6-hexanediisocyanate
HDI: hexamethylene diisocyanate
IEM: methacryloxyethyl isocyanate
ICEM: 1-methacryloxyethyl-2,4,4(2,2,4)-trimethyl-6-hexaneisocyanate
CDI: 1,1'-carbonyldiimidazole
BHT: butylhydroxytoluene
DBTDL: dibutyltin dilaurate
TCDCA: tricyclo[$5.2.1.0^{2,6}$]decane-dimethanol diacrylate
TPH/A2: A2 shade of universal composite from DENTSPLY
EsthetX/A2: A2 shade of universal composite from DENTSPLY
SureFil/A: A shade posterior composite from DENTSPLY;
Filtek Supreme/A2B: A2B shade universal composite from 3M;
Filtek Supreme/YT: 17 shade of universal composite from 3M:
Harpoon/A2/A3.5/B1/B3/CE: Experimental posterior composite from DENTSPLY
Virtuoso/A2: Flowable composite from Denmat
DyractFlow/A4: Flowable composite from DENTSPLY
Filtek SP Flow: Flowable composite from 3M BASE Resin Example 1

Preparation of the Adduct of ICEM-HP-ICEM

A 500 ml three-necked flask equipped with a mechanical agitator, dry air inlet and water-cooling condenser, which was immersed in an oil-bath, was charged 56.3 grams of ICEM, and 20.0 grams of TEGDMA. Then 0.11 gram of DBTDL and 0.05 gram of BHT. The bath temperature was set at 25° C. Then it was added all of 11.2 grams of grounded Irgacure 2959 powder. The reaction occurred slowly as evident by the slow temperature increase. Heated up to 35° C. and kept for additional 222 hrs prior to reach its maximum conversion of 96% as liquid resin.

Base Resin Example 2

Preparation of the Adduct of HEMA-HMDI-HP-HMDI-HEMA

A 250 ml three-necked flask equipped with a powder addition funnel, mechanical agitator, dry air inlet and water-cooling condenser, which was immersed in an oil-bath, was charged 40.8 grams of HDI, and 0.17 gram of DBTDL and 0.15 gram of BHT. Then 22.4 grams of grounded Irgacure 2959 powder were slowly in portion added into the flask in a period of 3-4 hrs. The reaction temperature was remained at 25° C. through the step. The fully conversion of Irgacure 2959 powder as fully capped with TMDI can be easily determined by $^1$H NMR. With continuous purge of dry air into the reaction system, 27.0 grams of HEMA was slowly added into the flask. The reaction temperature was raised to 35-40° C. After additional 6 hrs reaction at 35-40° C., 70 grams of diluent, was mixed with the resulting resin for a couple of hours prior to discharge.

Base Resin Example 3

Preparation of the Adduct of HEMA-TMDI-HP-TMDI-HEMA

A 1000 ml jacked, cylinder resin kettle equipped with a powder addition funnel, mechanical agitator, dry air inlet and water-cooling condenser, through which 35° C. of heated water was circulated during the reaction, was charged 96.6 grams of TMDI, and 0.25 gram of DBTDL. Then 35.5 grams of grounded Irgacure 2959 powder were slowly in portion added into the flask in a period of 6 hrs. The fully conversion of HP as fully capped with TMDI can be easily determined by $^1$H NMR. Then 0.20 gram of BHT was charged into the system. With continuous purge of dry air into the reaction system, 86.2 grams of HEMA was added into the flask through a dropping funnel during a period of 2 hrs. An effective agitation is critical during the initial stage of HEMA addition in order to minimize the reaction rate so as to avoid overheat in the system, which can cause premature polymerization or gelation. The reaction temperature has to be controlled below 60° C., best for below 45° C. After HEMA addition, allow for additional 1 hr reaction at 35-40° C. Then additional diluent such as 30-40 grams of TEGDMA was charged into system and mixed for a couple of hours. Liquid resin was resulted with yield of 97-99%.

TABLE I

Composition of Base Resins

| Base Resin | diol | Isocyanate | Hydroxylated Methacrylate | Diluent |
| --- | --- | --- | --- | --- |
| Base Resin 1 | Irgacure 2959 | ICEM | | TCDCA |
| Base Resin 2 | Irgacure 2959 | TMDI | HEMA | TEGDMA |
| Base Resin 3 | Irgacure 2959 | HMDI | HPMA | TEGDMA |

Formulated Resin Example 1 through 7

In Table II it was listed various formulated resins were further formulated from the Base Resins as made from the procedures described above.

TABLE II

Formulated Resins with Different Compositions

| Formulated Resin | Base Resin 1 (B-1) Base Resin 2 (B-2) Base Resin 3 (B-3) (%, wt/wt) | EBPADMA(E) BisGDMA(B) Macrocyclic Resin(M) TPH Resin(TP) (%, wt/wt) | TEGDMA(T) UDMA(U) TCDCMA(TC) (%, wt/wt) |
| --- | --- | --- | --- |
| F- Resin 1 | B-1: 60 | M: 20 | U: 20 |
| F- Resin 2 | B-1: 60 | M: 30 | T: 10 |
| F- Resin 3 | B-3: 60 | TP: 30 | TC: 10 |
| F- Resin 4 | B-3: 80 | TP: 20 | |
| F- Resin 5 | B-3: 80 | | TC: 10 |
| | | | T: 10 |
| F- Resin 6 | B-3: 85 | | T: 15 |
| F- Resin 7 | B-3: 85 | | T: 15 |
| F- Resin 8 | B-1: 50 | M: 35 | U: 15 |
| F- Resin 9 | B-1: 50 | M: 50 | |
| F- Resin 10 | B-2: 85 | | T: 15 |
| F- Resin 11 | B-2: 70 | E: 15 | T: 15 |

Typical Composite Compounding Process

All the pre-weighed resin blend and filler blend were put into the mixer container and compounded for 10-20 minutes at 50° C. Then the mixer container and mixer blades were scraped so that all fillers were wetted by the resin. The paste were compounded under 20-27 in Hg vacuum for 20-40 minutes.

Formulated Composites Example 1 through 13

In Table III it was listed different formulated composites from various formulated resins.

TABLE III

Formulated Composites with Different Compositions

| Formulated Composite | Formulated Resin (%, wt/wt) | Filler Bland: 1, AeroSil R972; 2, Fumed silica OX50; 3, Strontium Aluminosilicate Glass; 4, Barium FluoroAluminoboroasilcate glass; 5, Barium Aluminoboroasilcate glass; (%, wt/wt) |
|---|---|---|
| Composite 1 | F-8: 18.4 | 81.6(1/4) |
| Composite 2 | F-9: 18 | 82(1/4) |
| Composite 3 | F-2: 18 | 82(1/4) |
| Composite 4 | F-6: 18 | 82(1/4) |
| Composite 5 | F-7: 18.5 | 81.5(1/4) |
| Composite 6 | F-6: 40 | 60(1/4) |
| Composite 7 | F-7: 40 | 60(1/4) |
| Composite 8 | F-7: 40 | 60(1/4/2) |
| Composite 9 | F-7: 40 | 60(1/4/2) |
| Composite 10 | F-7: 40 | 60(1/4/2) |
| Composite 11 | F-7: 40 | 60(1/4/2) |
| Composite 12 | F-7: 40 | 60(1/4/2) |
| Composite 13 | F-7: 40 | 60(1/4/2) |
| Composite 14 | F-7: 40 | 60(1/4/2) |
| Composite 15 | F-7: 40 | 60(1/4/2) |
| Composite 16 | F-6: 40 | 60(1/4/2) |
| Composite 17 | F-6: 40 | 60(1/4) |
| Composite 18 | F-6: 40 | 60(1/4/2) |
| Composite 19 | F-6: 40 | 60(1/4) |
| Composite 20 | F-11: 32 | 68(3/4) |
| Composite 21 | F-11: 32 | 68(3/4) |
| Composite 22 | F-11: 32 | 68(1/3/4) |
| Composite 23 | F-11: 32 | 68(1/3/4) |

TABLE IV

Polymerization Shrinkage and Stress for Various Activated Resins

| | | Shrinkage (%) by Helium Pycnometer | Stress (MPa) by Tensometer |
|---|---|---|---|
| Conventional Resins | Urethane-modified BisGMA(TPH Resin 1) | 6.8 | 4.5 |
| | Urethane-modified BisGMA(TPH Resin 2) | 7.3 | 4.3 |
| | Macrocyclic Methacrylate 1 | 5.5 | 3.1 |
| | Macrocyclic Methacrylate 2 | 5.8 | 3.2 |
| Resins | F-1 | 5.2 | 1.4 |
| | F-2 | 5.7 | 2.0 |
| | F-3 | 6.5 | 1.9 |
| | F-4 | 6.2 | 1.5 |
| | F-5 | 6.9 | 1.5 |

TABLE V

Physical Property for Activated Resin Systems

| | F-6 | F-7 |
|---|---|---|
| Viscosity at 20° C., poise | 1050 | 1020 |
| Uncured density, g/cm$^3$ | 1.1164 | 1.1162 |
| Cured density, g/cm$^3$ | 1.1865 | 1.1867 |
| Shrinkage @ 24 hrs, % | 5.91 | 5.96 |
| Stress @ 60 min, MPa | 1.6 | 1.4 |

TABLE VI

Polymerization Shrinkage and Stress for Various Composites

| | Composites | Shrinkage (%) by Helium Pycnometer | Stress (MPa) by Tensometer |
|---|---|---|---|
| Commercial Products based on Conventional Resins | TPH/A2 | 3.10 | 2.9 |
| | EsthetX/A2 | 2.92 | 2.5 |
| | SureFil/A | 2.09 | 2.7 |
| | Supreme/A2B | 2.65 | N/A |
| | Supreme/YT | 2.39 | N/A |
| Experimental Composite based on Macrocyclic Resins | Harpoon/A2 | 1.34 | 1.7 |
| | Harpoon/A3.5 | 1.70 | 1.8 |
| | Harpoon/B1 | 1.31 | 1.5 |
| | Harpoon/B2 | 1.61 | 1.9 |
| | Harpoon/CE | 1.70 | 1.9 |
| Experimental Composite based on Resins | Composite 1 w/F-8 | 0.87 | 1.5 |
| | Composite 2 w/F-9 | 0.93 | 1.4 |
| | Composite 3 w/F-2 | 0.36 | 1.4 |

TABLE VII

Property of Resin-based Composites with Variable Fillers

| Pastes | Composite 4 | Composite 5 | Composite 6 | Composite 7 |
|---|---|---|---|---|
| Shrinkage (%) by pycnometer @ 20 hrs later | 1.6 | 1.8 | 3.6 | 3.5 |
| Shrinkage Stress (MPa) by tensometer | 1.4 | 1.6 | 0.9 | 0.9 |
| Flexural Strength (MPa) | 137 +/− 4 | 128 +/− 9 | 109 +/− 6 | 109 +/− 5 |
| Modulus(MPa) | 10800 +/− 440 | 9963 +/− 136 | 4700 +/− 190 | 4600 +/− 110 |
| Compressive Strength (MPa) | 344 +/− 11 | 316 +/− 24 | 277 +/− 13 | 283 +/− 3 |
| Modulus(MPa) | 8080 +/− 530 | 7920 +/− 214 | 4900 +/− 450 | 5260 +− 330 |

TABLE VIII

Composition and Polymerization Stress for Resin-based Low Viscosity Composites

| Pastes | Polymerization Stress @60 min MPa |
|---|---|
| Control Composite w/TPH resin | 3.53 |
| Composite 8 w/F-7 | 0.92 |
| Composite 9 w/F-7 | 0.97 |
| Composite 10 w/F-7 | 1.00 |
| Composite 11 w/F-7 | 1.10 |
| Composite 12 w/F-7 | 1.22 |
| Composite 13 w/F-7 | 1.32 |
| Composite 14 w/F-7 | 1.18 |
| Composite 15 w/F-7 | 1.05 |
| Composite 16 w/F-6 | 1.13 |
| Composite 17 w/F-6 | 1.11 |
| Composite 18 w/F-6 | 1.39 |
| Composite 19 w/F-6 | 1.31 |

TABLE IX

Comparative Commercially-available Flowable Composites

| | Virtuoso Flow/A2 | DyractFlow/A4 | FiltekSPFlow |
|---|---|---|---|
| Resin by weight (%) | 47 | 40.6 | 35 |
| Total Filler by weight (%) | 53 | 59.4 | 65 |
| ISO Depth of Cure (mm) | 2.4 | 2.1 | 2.5 |
| Volumetric Shrinkage (%) | 3.9 | 6.3 | 4.6 |
| Polymerization Stress (MPa) | 1.6 | >4.2 | 3.9 |
| Flexural Strength (MPa) | 64 | 100 | 124 |
| Flexural Modulus (GPa) | 2.8 | 4.3 | 5.1 |
| Compressive Strength (MPa) | 254 | 315 | 354 |
| Viscosity @ 35° C. & 10 Pa Shear Stress (Pa · s) | 338 | 152 | 7906 |
| Flow Characteristics | Self-Leveling | Self-Leveling | Stackable |

TABLE X

Experimental Examples

| | Composite Example 20 | Composite Example 21 | Composite Example 22 | Composite Example 23 |
|---|---|---|---|---|
| Formulated Resin 8 by weight (%) | 32 | 32 | 32 | 32 |
| I Filler Blend by weight (%) | 68 | 68 | 68 | 68 |
| ISO Depth of Cure (mm) | 4.7 | 4.7 | 4.6 | 4.1 |
| Opacity | 30 | 27 | 27 | 40 |
| Volumetric Shrinkage (%) | 3.7 | 3.5 | 3.6 | 3.5 |
| Polymerization Stress (MPa) | 1.7 | 1.7 | 1.6 | 1.6 |
| Flexural Strength (MPa) | 109 | 114 | 110 | 115 |
| Flexural Modulus (GPa) | 6.1 | 6.1 | 5.8 | 5.8 |
| Compressive Strength (MPa) | 226 | 228 | 233 | 242 |
| Viscosity @ 35° C. & 10 Pa Shear Stress (Pa · s) | 33520 | 1734 | 148 | 397 |
| Flow Characteristics | Stackable | Semi-stackable | Self-Leveling | Self-Leveling |

TABLE XI

Primary Components for Low Viscosity and Low Stress Composites

| Component | Chemical Name | Function | Wt % |
|---|---|---|---|
| Resin | Oliogmers of diisocyanate and hydroxyl propyl methacrylate and Irgacure 2959 | Polymerizable resin matrix | 15 |
| EBPADMA | 2-Methyl-acrylic acid 2-(2-{4-[1-methyl-1-(4-{2-[2-(2-methyl-acryloyloxy)-ethoxy]-ethoxy}-phenyl)-ethyl]-phenoxy}-ethoxy)-ethyl ester | Polymerizable resin matrix | 5 |
| UDMA | 1,6-Bis(methacryloxy-2-propoxycarbonylamino)hexane | Polymerizable resin matrix | 10 |
| TEGDMA | 2-Methyl-acrylic acid 2-{2-[2-(2-methyl-acryloyloxy)-ethoxy]-ethoxy}-ethyl ester | Polymerizable resin matrix | 5 |
| Silanated BAFG Glass | ☒-Methacryloxypropyltrimethoxysilane surface treated barium fluoro alumino borosilicate glass | Filler | 20 |

TABLE XI-continued

Primary Components for Low Viscosity and Low Stress Composites

| Component | Chemical Name | Function | Wt % |
|---|---|---|---|
| Silanated Strontium Aluminosilicate Glass | Strontium alumino sodium fluoro silicate | Filler | 44 |
| Aerosil R-972 | Fumed Silica (SiO$_2$) | Filler | 1 |

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

We claim:

1. A dental composition, comprising:
an oligomeric resin, a second resin, and a filler comprising a mixture of fumed silica, strontium aluminosilicate glass, and barium fluoroaluminoborosilicate glass,
wherein the oligomeric resin is made of a hydroxylated (meth)acrylate, a polyisocyanate, and a reactive monomer with photoresponsive moiety derived from a reactive photoinitiator,
wherein the dental composition has an initial viscosity of under a low shear stress of about 10 Pa in a range of from about 10 Pa s to about 1000 Pa s at about 35° C.,
wherein the dental composition has a depth of cure of from about 3 mm to about 6 mm, and
wherein the dental composition has a polymerization stress of from about 0.5 MPa to about 2 MPa.

2. The dental composition of claim 1, wherein the hydroxylated (meth)acrylate is present in the oligomeric resin in amounts of from about 25 weight percent to about 60 weight percent, the polyisocyanate is present in the oligomeric resin in amounts of from about 30 weight percent to about 60 weight percent, and the reactive monomer with photoresponsive moiety is present in the oligomeric resin in amounts of from about 25 weight percent to about 60 weight percent.

3. The dental composition of claim 1, wherein the reactive photoinitiator is 1-[4-(2-hydroxyethoxy)-phenyl]-2-hydroxy-2-methyl-1-propanone-1-one.

4. The dental composition of claim 1, wherein the (meth)acrylate is a monohydroxylated (meth)acrylate selected from the group consisting of hydroxyethyl acrylate, hydroxypropyl acrylate, hydroxyethyl methacrylate, and hydroxypropyl methacrylate.

5. The dental composition of claim 1, wherein the polyisocyanate is 2,4-toluene diisocyanate (TDI), 2,6-toluene diisocyanate, diphenylmethane 4,4'-diisocyanate (MDI), diphenylmethane 2,4'-diisocyanate, 1,5-diisocyanato-naphthalene, 1,4-phenylene diisocyanate, 1,3-phenylene diisocyanate, 1-methyoxy-2,4-phenylene diisocyanate, 1-chlorophenyl-2,4-diisocyanate, dicyclohexylmethane diisocyanate (H$_{12}$MDI), 4,4'-isopropyl-bis(cyclohexylisocyanate), isophorone diisocyanate (IPDI), cyclobutane-1,3-diisocyanate, cyclohexane 1,3-diisocyanate, cyclohexane 1,4-diisocyanate (CHDI), 1,4-cyclohexanebis(methylene isocyanate) (BDI), dimmer acid diisocyanate, 1,3-bis(isocyanatomethyl)cyclohexane (H$_6$XDI), 3-isocyanatomethyl-3,5,5-trimethylcyclohexyl isocyanate, tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, 2,2,4-trimethyl-hexamethylene diisocyanate (TMDI), 2-methyl-1,5-pentamethylene diisocyanate, dimer diisocyanate, a urea of hexamethylene diisocyanate, a biuret of HDI, an isocyanurate of HDI, a blend of the isocyanurate of HDI and a uretdione of HDI, m-tetramethyl xylylene diisocyanate (m-TMXDI), p-tetramethyl xylylene diisocyanate (p-TMXDI), 1,4-xylylene diisocyanate (XDI), 1,3-xylylene diisocyanate, p-(1-isocyanatoethyl)phenyl isocyanate, m-(3-isocyanatobutyl)phenyl isocyanate, 4-(2-isocyanatocyclohexyl-methyl)phenyl isocyanate, xylylene-1,4-diisocyanate (p-XDI), xylylene-1,3-diisocyanate (m-XDI), m-pheylene diisocyanate, p-pheylene diisocyanate, toluene-2,6-diisocyanate (2,6-TDI), toluene-2,4-diisocyanate (2,4-TDI), mesitylene diisocyanate, durylene diisocyanate, benzidene diisocyanate, 1-methyl phenylene-2,4-diisocyanat; naphthylene-1,4-diisocyanate, 1,2,4-benzene triisocyanate, 4,4'-diisocyanato diphenyl methane (MDI), 3,3'-dimethyl-4,4'-diisocyanato diphenyl methane, 4,4'-diphenyl propane diisocyanate, dianisidine diisocyanate, m-tetramethylenexylene diisocyanate (TMXDI), or mixtures thereof.

6. The dental composition of claim 1, wherein the second resin is selected from the group consisting of methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, trishydroxyethyl-isocyanurate trimethacrylate, (meth)acrylamides, methylene bis-(meth)acrylamide, and diacetone (meth)acrylamide, urethane (meth)acrylates, bis-(meth)acrylates of polyethylene glycols, copolymerizable mixtures of acrylated monomers, acrylated oligomers, poly(ethylenically unsaturated) carbamoyl isocyanurates, styrene, diallyl phthalate, divinyl succinate, divinyl adipate, divinyl phthalate, siloxane-functional (meth)acrylates, fluoropolymer-functional (meth)acrylates, hydroxyalkyl(meth)acrylates, 2-hydroxyethyl(meth)acrylate, 2-hydroxypropyl(meth)acrylate, glycerol mono-(meth)acrylate, glycerol di-(meth)acrylate, trimethylolpropane mono-(meth)acrylate, trimethylolpropane di-(meth)acrylat, pentaerythritol mono-(meth)acrylate, pentaerythritol di-(meth)acrylate, and pentaerythritol tri-(meth)acrylate, sorbitol mono-(meth)acrylate, sorbitol di-(meth)acrylate, sorbitol tri-(meth)acrylate, sorbitol tetra-(meth)acrylate, sorbitol penta-(meth)acrylate, 2,2-bis[4-(2-hydroxy-3-methacryloxypropoxy)phenyl]propane (bisGMA), polyethyleneglycol dimethacrylate, urethane dimethacrylate, glycerol dimethacrylate, triethyleneglycol dimethacrylate, neopentylglycol dimethacrylate, and mixtures thereof.

7. The dental composition of claim 1, further comprising a photoinitiator, a fluorescent agent, a colorant, or mixtures thereof.

8. The dental composition of claim 1, wherein the oligomeric resin and the second resin, in combination, are present in the dental composition in amounts of from about 10 weight percent to about 95 weight percent, and the filler is present in the dental composition in amounts of from about 5 weight percent to about 90 weight percent.

9. The dental composition of claim 1, wherein the composition is self-leveling.

10. A method of making a dental composition, comprising:
forming an oligomeric resin having a reactive monomer with photoresponsive moiety by combining a hydroxylated (meth)acrylate, a polyisocyanate, and a reactive photoinitiator,
combining the oligomeric resin and a second resin to form a compound resin, and
combining the compound resin with a filler comprising a mixture of fumed silica, strontium aluminosilicate glass, and barium fluoroaluminoborosilicate glass to form the dental composition,
wherein the dental composition has an initial viscosity of under a low shear stress of about 10 Pa in a range of from about 10 Pa s to about 1000 Pa s at about 35° C.,
wherein the dental composition has a depth of cure of from about 3 mm to about 6 mm,
wherein the dental composition has a polymerization stress of from about 0.5 MPa to about 2 MPa, and
wherein the dental composition has a shrinkage stress of from about 0.8 MPa to about 2.2 MPa.

11. The method of claim 10, wherein the amount of acrylate used in forming the oligomeric resin is from about 25 weight percent to about 60 weight percent, the amount of polyisocyanate used in forming the oligomeric resin is from about 30 weight percent to about 60 weight percent, and the amount of photoinitiator used in forming the oligomeric resin is from about 25 weight percent to about 60 weight percent.

12. The method of claim 10, wherein the initiator used in forming the oligomeric resin is 1-[4-(2-hydroxyethoxy)-phenyl]-2-hydroxy-2-methyl-1-propanone-1-one.

* * * * *